United States Patent
Beria et al.

(10) Patent No.: US 10,556,913 B2
(45) Date of Patent: Feb. 11, 2020

(54) ASYMMETRIC PROCESS FOR THE PREPARATION OF THIENO-INDOLES DERIVATIVES

(71) Applicant: NERVIANO MEDICAL SCIENCES S.R.L., Nerviano (IT)

(72) Inventors: Italo Beria, Nerviano (IT); Michele Caruso, Milan (IT); Daniele Donati, Nerviano (IT); Paolo Orsini, Legnano (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 16/177,551

(22) Filed: Nov. 1, 2018

(65) Prior Publication Data

US 2019/0071451 A1    Mar. 7, 2019

Related U.S. Application Data

(62) Division of application No. 15/745,852, filed as application No. PCT/EP2016/066533 on Jul. 12, 2016.

(30) Foreign Application Priority Data

Jul. 21, 2015   (EP) ..................... 15177734

(51) Int. Cl.
   *C07D 495/04*   (2006.01)
(52) U.S. Cl.
   CPC .................. *C07D 495/04* (2013.01)
(58) Field of Classification Search
   CPC .................................................. C07D 495/04
   See application file for complete search history.

(56) References Cited

U.S. PATENT DOCUMENTS 9,527,863 B2    12/2016   Beria et al.
2018/0215768 A1   8/2018   Beria et al.

FOREIGN PATENT DOCUMENTS

| GB | 2 344 818 A | 6/2000 |
| WO | 02/083180 A1 | 10/2002 |
| WO | 2004/043493 A1 | 5/2004 |
| WO | 2013/149946 A1 | 10/2013 |
| WO | 2013/149948 A1 | 10/2013 |

OTHER PUBLICATIONS

Blencowe C.A. et al., "Self-Immolative Linkers in Polymeric Delivery Systems", Polym. Chem. 2:773-790 (2011).
Elgersma R.C. et al., "Design, Synthesis, and Evaluation of Linker-Duocarmycin Payloads: Toward Selection of HER2-Targeting Antibody-Drug Conjugate SYD985", Mol. Pharmaceutics 12:1813-1835 (2015).
Lajiness J.P. et al., "Asymmetric Synthesis of 1,2,9,9a-Tetrahydrocycloapropa[c]Benzo[e]Indol-4-One (CBI)", J Org Chem. 76(2):583-587 (Jan. 21, 2011).
Muratake H. et al., "Preparation of Benzene, Furan, and Thiophene Analogs of Duocarmycin SA Employing a Newly-Devised Phenol-Forming Reaction", Chem. Pharm. Bull. 48(10):1558-1566 (2000).
Tichenor M.S. et al., "Rational Design, Synthesis, and Evaluation of Key Analogues of CC-1065 and the Duocarmycins", J Am Chem Soc. 129(45):14092-14099 (Nov. 14, 2007).
Tranoy-Opalinski I. et al., "Design of Self-Immolative Linkers for Tumour-Activated Prodrug Therapy", Anti-Cancer Agents in Medicinal Chemistry 8:618-637 (2008).
Uematsu M. et al., "Asymmetric Synthesis of a CBI-Based Cyclic N-Acyl O-Amino Phenol Duocarmycin Prodrug", The Journal of Organic Chemistry 9699-9703 (2014).
International Search Report dated Sep. 29, 2016 received in International Application No. PCT/EP2016/066533.

*Primary Examiner* — Golam M Shameem
(74) *Attorney, Agent, or Firm* — Scully, Scott, Murphy & Presser, P.C.

(57) ABSTRACT

The present invention relates to a new process for the preparation of thieno-indole derivatives of formula (Ia) or (Ib), exploiting an asymmetric synthesis for the preparation of key (8S) or (8R) 8-(halomethyl)-1-alkyl-7,8-dihydro-6H-thieno[3,2-e]indol-4-ol intermediates, and to useful intermediate compounds of such process.
Thieno-indole derivatives are described and claimed in GB2344818, WO2013/149948 and WO2013/149946, which also disclose processes for their preparation.
Thieno-indole enantiopure derivatives can now be advantageously prepared through a new asymmetric synthesis of the key 8-(halomethyl)-7,8-dihydro-6H-thieno[3,2-e]indol intermediates, which, avoiding the chiral resolution step, provides benefits in terms of reducing time and costs of the whole process for their preparation. The synthesis starts from the N-alkylation of 5-amino-4-halo-3-alkyl-1-benzothiophene-7-ol derivatives with enantiopure glycidyl 3-nosylate, followed by intramolecular 6-endo-tet cyclization using alkyl Grignard reagents; Mitsunobu activation of the secondary alcohol promotes internal spirocyclization, affording the 4,4a,5,6-tetrahydro-8H-cyclopropa[c]thieno[3,2-e]indol-8-one derivatives; finally, stereo-electronically controlled regioselective cyclopropane opening yields the key enantiopure 8-(halomethyl)-1-alkyl-7,8-dihydro-6H-thieno[3,2-e]indol-4-ol intermediates; which can be further derivatized following teachings disclosed in WO2013/149948 or WO2013/149946, to prepare the final thieno-indole derivatives of formula (Ia) or (Ib).
Such compounds are disclosed to be alkylating compounds with cytotoxic activity, therefore useful as such in the treatment of a variety of cancers and in cell proliferative disorders, or, conjugated with different types of nucleophiles, in the preparation of Antibody Drug Conjugated derivatives.

5 Claims, No Drawings

ASYMMETRIC PROCESS FOR THE PREPARATION OF THIENO-INDOLES DERIVATIVES

CROSS REFERENCE TO RELATED APPLICATIONS

The present application is a divisional of co-pending application having U.S. Ser. No. 15/745,852, filed on Jan. 18, 2018, which is a 371 of International Application No. PCT/EP2016/065533, filed on Jul. 12, 2016, which claims priority to European Patent Application No. 15177734.9, filed on Jul. 12, 2016, the contents of all of which are incorporated here by reference.

The present invention relates to a new process for the preparation of thieno-indole derivatives of formula (Ia) or (Ib), exploiting an asymmetric synthesis for the preparation of key (8S) or (8R) 8-(halomethyl)-1-alkyl-7,8-dihydro-6H-1-thieno[3,2-e]indol-4-ol intermediates, and to useful intermediate compounds of such process.

Thieno-indole derivatives are described and claimed in GB2344818, WO2013/149948 and WO2013/149946, which also disclose processes for their preparation, pharmaceutical composition comprising them and use thereof in treating certain mammalian tumors.

Such compounds are described as alkylating compounds with cytotoxic activity, thus useful as such in the treatment of a variety of cancers and in cell proliferative disorders. Additionally, the same compounds are also suitable for conjugation with different types of nucleophiles and are thus useful in the preparation of e.g. Antibody Drug Conjugates derivatives.

These thieno-indole derivatives, and analogues thereof, can be prepared according to known chemical processes, such as, for instance, following the preparation reported in *J. Am. Chem. Soc.* 2007, 129, 14092-14099. In particular, the synthesis of enantiopure thieno-indole derivatives disclosed in the above cited prior art documents was carried out through a process wherein the enantiopure., key 8-(halomethyl)-1-alkyl-7,8-dihydro-6H-thieno[3,2-e]indol-4-ol intermediates were obtained by chiral resolution from a racemic mixture, performed by reverse phase chiral chromatography, with the involvement of time consuming and expensive steps.

In this respect, we have now surprisingly found that said enantiopure key 8-(halomethyl)-1-alkyl-7,8-dihydro-6H-thieno[3,2-e]indol-4-ol intermediates can advantageously be prepared by an asymmetric synthesis which, avoiding the chiral resolution step, provides benefits in terms of reducing time and costs of the whole process for the preparation of final thieno-indole derivatives, as it prevents loss of material when just one of the two enantiomers of the final compound has to be prepared. Additionally, the new process shows higher overall yield with respect to the previous known processes.

Examples of asymmetric synthesis, but performed to obtain phenyl-indole analogues of the duocarmycin DNA alkylation subunits, are reported in the literature, see e.g. *Mol. Pharmaceutics* 2015, 12, 1813-1835, *J. Org. Chem.* 2011, 76, 583-587 and *J. Org. Chem.* 2014, 79, 9699-9703.

However, the synthesis approach reported in Mol. Pharmaceutics leads in some cases to the formation of undesired by-products which requires the addition of further purification and separation steps. This drawback is minimized by the present invention, probably due to the use of less basic reaction conditions.

Furthermore, with respect to *J. Org. Chem.* papers, the presence of the alkyl thiophene ring of the present invention, less reactive and more electron-rich than the phenyl ring, surprisingly allows the use of milder reaction conditions for the cyclization step, which is driven by the insertion of the Grignard reagent into the C—I bond, Therefore, it is a first object of the present invention a process for preparing thieno-indole derivatives of formula (Ia) or (Ib):

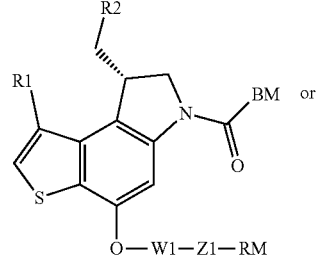

(Ia)

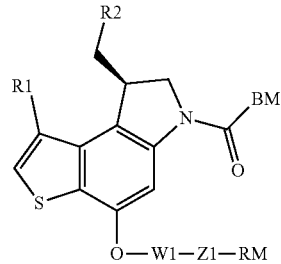

(Ib)

wherein:
R1 is hydrogen or linear or branched $C_1$-$C_8$ alkyl;
R2 is a leaving group selected from halogen and sultanate groups;
BM is a DNA binding moiety of formula (II-1) or (II-2):

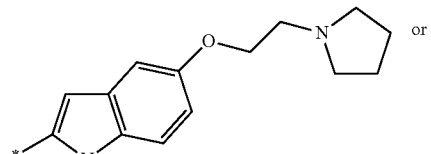

(II-1) or

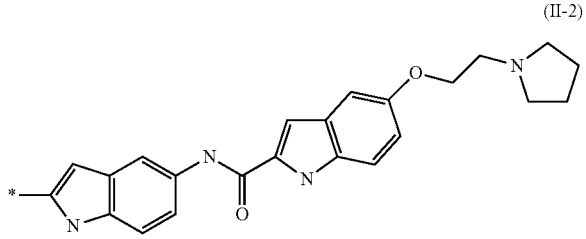

(II-2)

W1 is a self-immolative system of formula (III):

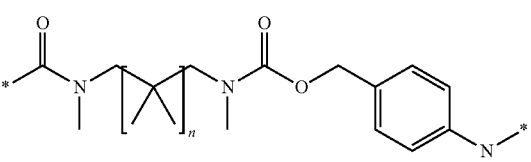

(III)

wherein n is 0 or 1;
Z1 is a linker of formula (IV-1) or (IV-2):

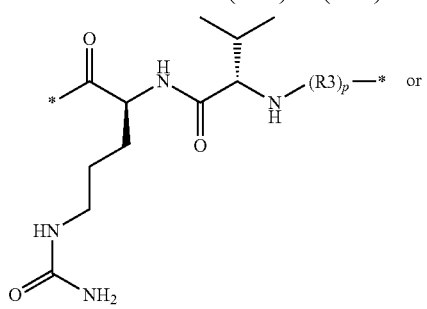

(IV-1) or (IV-2)

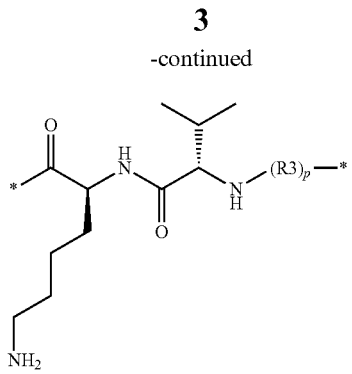

wherein p is an integer from 0 to 1 and R3 is a polyoxyethylenic chain of formula (V):

(V)

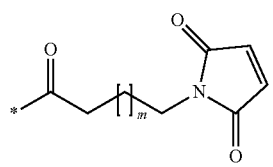

wherein m is an integer from 0 to 5; and
RM is a reactive moiety of formula (VI):

(VI)

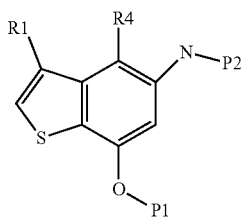

wherein m is as defined above;
which process comprises the following steps:
Step a) alkylating a compound of formula (VII):

(VII)

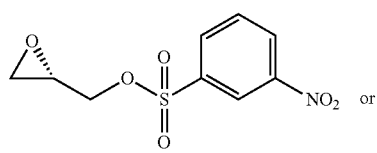

wherein R4 is halogen, P1 is a hydroxyl protecting group, P2 is a nitrogen protecting group and R1 is as defined above, with (S)-glycidyl 3-nosylate (VIIIa) or (R) glycidyl 3-nosylate (VIIIb):

(VIIIa)

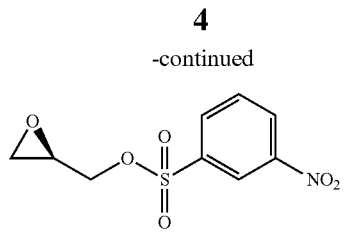

or (VIIIb)

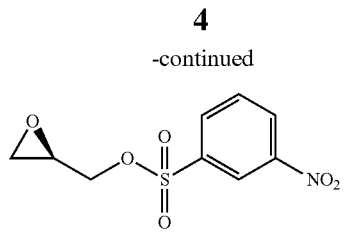

Step reacting the resulting compound of formula (IXa) or (IXb):

(IXa)

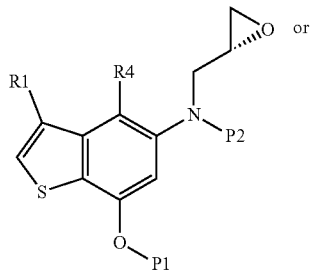

or (IXb)

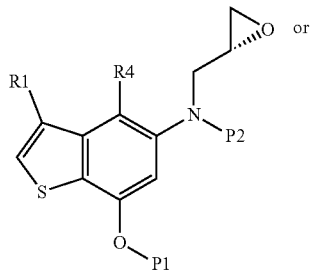

wherein R1, R4, P1 and P2 are as defined above, with a metallo-organic reagent;

Step c) removing the hydroxyl protecting group P1 from the resulting compound of formula (Xa) or (Xb):

(Xa)

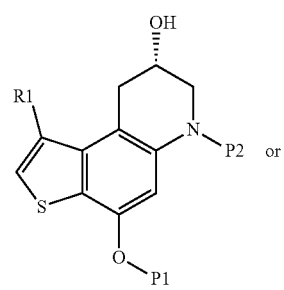

or (Xb)

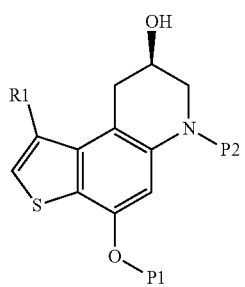

wherein R1, P1 and P2 are as defined above;

Step d) performing an internal spirocyclization of the resulting compound of formula (XIa) or (XIb):

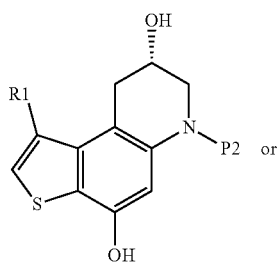
(XIa)

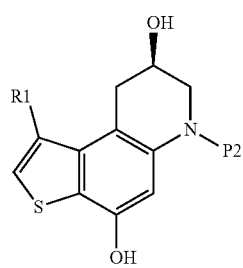
(XIb)

wherein R1 and P2 are as defined above;

Step e) obtaining a stereocontrolled regioselective cyclopropane opening of the resulting of formula (XIIa) or (XIIb)

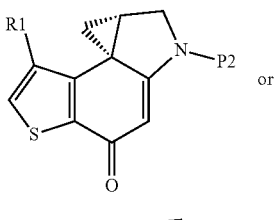
(XIIa)

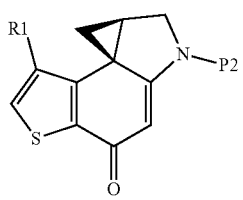
(XIIb)

wherein R1 and P2 are as defined above, by reaction with an acid of formula HR2, wherein R2 is as defined above;

Step f) removing the nitrogen protecting group P2 from the resulting compound of formula (XIIIa) or (XIIIb)

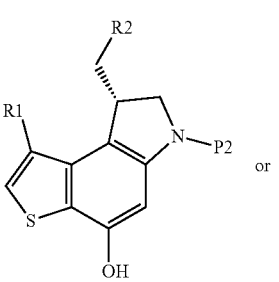
(XIIIa)

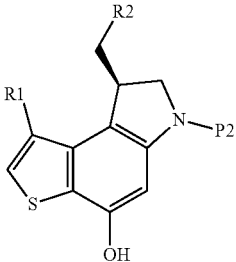
(XIIIb)

wherein R1, R2 and P2 are as defined above, thus obtaining the key enantiopure 8-(halomethyl)-1-alkyl-7,8-dihydro-6H-thieno[3,2-e]indol-4-ol intermediate of formula (XIVa) or (XIVb) respectively

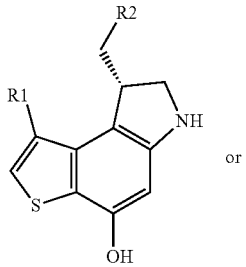
(XIVa)

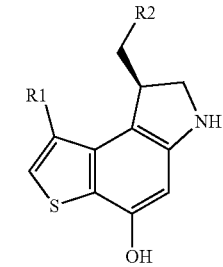
(XIVb)

wherein R1 and R2 are as defined above;

Step g) coupling the intermediate of formula (XIVa) or (XIVb) with the acid BM-COOH residue, thus obtaining the intermediate of formula (XVa) or (XVb) respectively

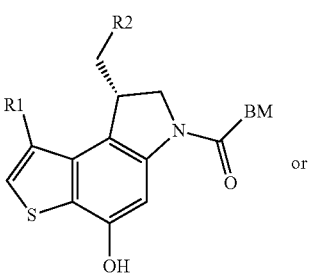
(XVa)

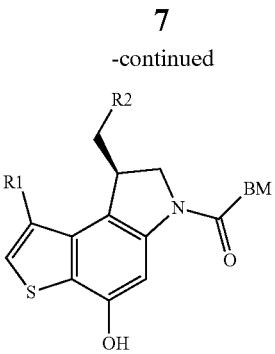

(XVb)

wherein BM, R1 and R2 are as defined above.

It is also object of the present invention the above asymmetric synthesis which further comprises derivatizing the intermediate of formula (XVa) or (XVb) at the phenol moiety according to the preparations and processes disclosed in the prior art references, such as those reported in WO2013/149948 on page 63 (step e'''), to yield the final thieno-indole derivatives of formula (Ia) or (Ib).

More clearly, it is also object of the present invention the above asymmetric synthesis which further comprises the following steps:

Step h) converting the intermediate of formula (XVa) or (XVb) into a carbonate derivative of formula (XVIa) or (XVIb) respectively

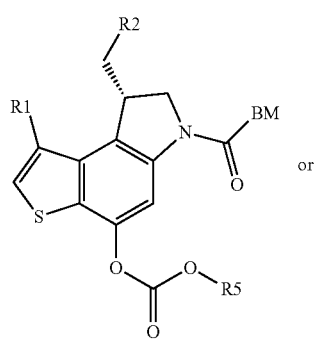

(XVIa)

or

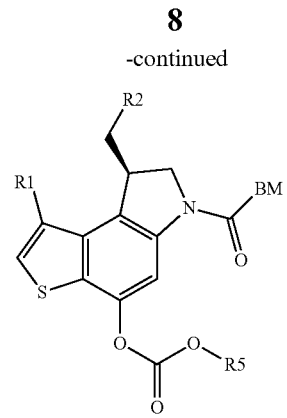

(XVIb)

wherein BM, R1 and R2 are as defined above and R5 is a succinimidyl or 4-nitro-phenyl residue;

Step i) reacting the resulting intermediate of formula (XVIa) or (XVIb) with an amine of formula (XVII)

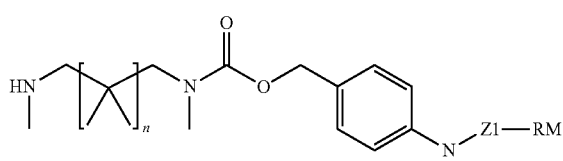

(XVII)

wherein n, Z1 and RM are as defined above, thus obtaining the final compounds of formula (Ia) or (Ib) respectively wherein R1, R2, BM, W1, Z1 and RM are as defined above.

Optionally, the resulting compounds of formula (Ia) or (Ib) as defined above can be converted into pharmaceutical acceptable salts.

The compounds of formula (Ia) or (Ib) as defined above, or the pharmaceutically acceptable salts thereof, can be subsequently formulated with a pharmaceutically acceptable carrier or diluent to provide a pharmaceutical composition.

The new process object of the present invention is shown in the following Scheme 1 relating to the synthesis of the enantiomer of formula (Ia):

Scheme 1

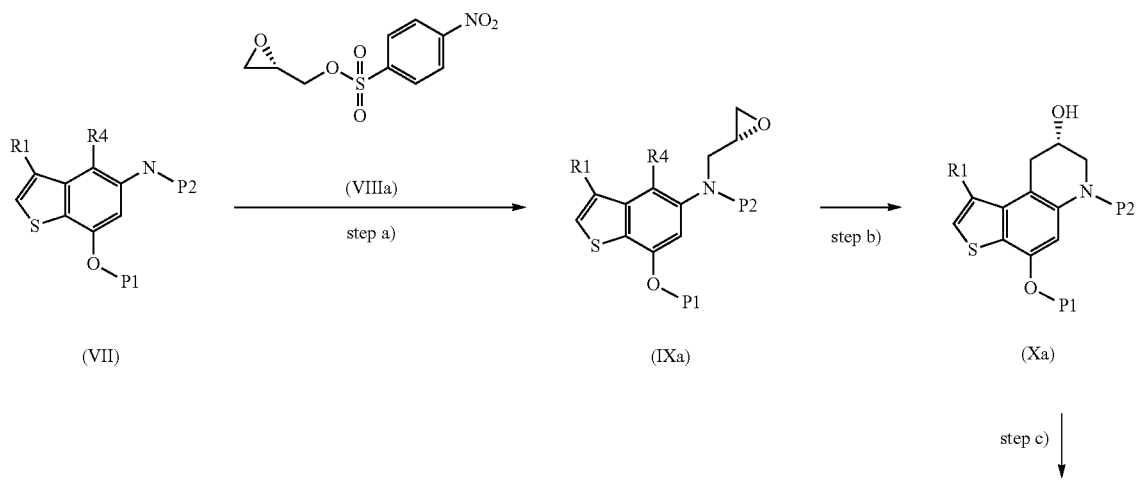

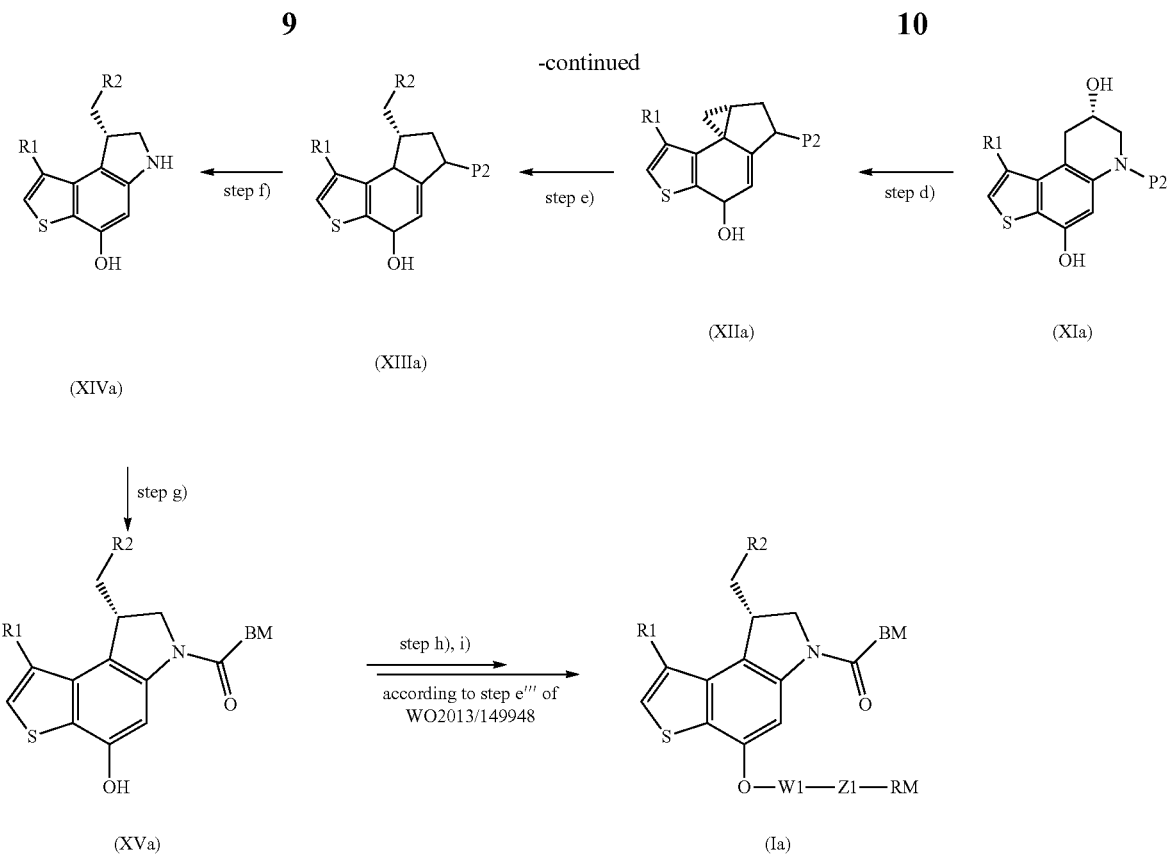

(XIVa) (XIIIa) (XIIa) (XIa)

(XVa) (Ia)

wherein R1, R2, R4, P1, P2, BM, W1, Z1 and RM are as defined above.

The synthesis starts from the N'-alkylation of a 5-amino-4-halo-3-alkyl-1-benzothiophene-7-ol derivative with enantiopure commercial glycidyl 3-nosylate (VIIIa, Step a), followed by intramolecular 6-endo-tet cyclization using alkyl Grignard reagents to give the enantiopure 6,7,8,9-tetrahydrothieno[3,2-f]quinolin-8-ol derivative (Xa, Step b); removal of the hydroxyl protecting group (Step c) followed by Mitsunobu activation of the secondary alcohol (Step d) promotes internal spirocyclization, affording the 4,4a,5,6-tetrahydro-8H-cyclopropa[c]thieno[3,2-e]indol-8-one derivative Step d); then, stereo-electronically controlled regioselective cyclopropane opening (Step e) followed by removal of the amino protecting group yields the key enantiopure 8-(halomethyl)-1-alkyl-7,8-dihydro-6H-thieno[3,2-e]indol-4-ol intermediate (XIVa, Step f); finally, coupling with the suitable acid BM-COOH residue affords the intermediate (XVa) (Step g).

The intermediate compounds prepared according to the process of the present invention can then be further derivatized at the phenol following previous prior art teachings, such as those disclosed in WO2013/149948, to prepare the final thieno-indole derivatives of formula (Ia) or (Ib) (Steps h, i).

It is clear to the skilled person that, in the process, when the enantiomer glycidol derivative of formula (VIIIb) is used in the alkylation of the starting material (VII), a compound of formula (IXb) is obtained and consequently the other corresponding thieno-indol enantiomer of formula (Ib) is obtained.

It is also clear to the skilled in the art that when the P2 protecting group is an acid labile moiety, such as for example a t-butoxycarbonyl moiety, the key intermediates of formula (XIVa) or (XIVb) can be directly obtained from compound (XIIa) or (XIIb) according to step e) conditions.

It is to be noted that the hydroxyl, W1, Z1 and RM1 moieties are linked together through carbamate or amide bonds and that the fragments of formula (III), (Z1) and (VI) are always oriented so that it is respectively formed a carbamate bond between the hydroxyl and W1, an amide bond between W1 and Z1 (exploiting the terminal aniline function of W1) and an amide bond between Z1 and RM1.

Any intermediates and/or final compounds may be isolated and purified using conventional procedures, for example chromatography and/or crystallization and salt formation.

Moreover, the intermediate compounds of formula (XIa) or (XIb), useful for the asymmetric synthesis of the thieno-indole derivatives of formula (Ia) or (Ib) as defined above, as well as the process for their preparation are a further object of the present invention.

Unless stated otherwise, the following terms and phrases as used herein are intended to have the following meanings.

The term "leaving group" refers to a group that can be substituted by another group in a substitution reaction. Such leaving groups are well-known in the art and examples include, but are not limited to, a halide (fluoride, chloride, bromide and iodide) and a sulfonate (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate). The term "leaving group" also refers to a group that is eliminated as a consequence of an elimination reaction, e.g., an electronic cascade reaction or a spirocyclization reaction. In this instance, a halide or a sulfonate group may for example be used as a leaving group. Preferably, leaving groups are chlorine or bromide.

The term "halogen" refers to bromo, chloro, iodo or fluoro, more preferably chloro or iodo.

The term "$C_1$-$C_6$ alkyl" refers to straight or branched saturated aliphatic hydrocarbyl groups having from 1 to 6 carbon atoms; this term is exemplified by groups such as methyl, ethyl, n-propyl, iso-propyl, n-butyl, isobutyl, sec-butyl, t-butyl, and the like.

The term "protecting group" refers to a group used to protect reactive centers in a chemical synthesis, for example, a hydroxyl group (—OH), an amino group (—$NH_2$), a thiol group (—SH), a carbonyl group (—C=O), a carboxylic group (—COOH). Examples of protecting groups are those reported in the literature (see, for instance, Green, Theodora W. and Wuts, Peter G. M.—Protective Groups in Organic Synthesis, Third Edition, John Wiley & Sons Inc., New York (N.Y.), 1999).

The term "nitrogen protecting group" refers to a group that, together with the nitrogen atom, forms carbamates, amides, cyclic imides, N-alkyl and N-aryl amines. Such protecting groups are well-known in the art (see e.g. ibidem). Non limiting examples of carbamate protecting groups are, for instance, methyl and ethyl carbamate, 9-fluorenylmethyl carbamate (Fmoc), 2,2,2-trichloroethylcarbamate (Troc), t-butyl carbamate (BOC), vinyl carbamate (Voc), allyl carbamate (Alloc), benzyl carbamate (Cbz), p-nitrobenzyl carbamate and the like. Non limiting examples of amides are, for instance N-trichloroacetamide, N-trifluoroacetamide (TPA) and the like. Non limiting examples of cyclic imide protecting groups are, for instance, N-phthalimide, N-dithiasuccinoylimide (Dts) and the like. Non limiting examples of N-alkyl and N-aryl protecting groups are, for instance, N-allylamine, N-benzylamine and the like.

The term "hydroxyl protecting group" refers to a group that, together with the oxygen atom, forms ethers, esters, cyclic acetals or ketals. Such protecting groups are well-known in the art (see e.g. ibidem). Non limiting examples of ethers protecting groups are, for instance, alkyl ethers and benzyl ethers, such as methoxymethyl ether (MOM-OR), tetrahydropyranyl ether (THP-OR), allyl ether (Allyl-OR), benzyl ether (Bn-OR), triphenylmethyl ether (Tr-OR) and the like, or silyl ethers, such as trimethylsilyl ether (TMS-OR), t-butyldimethylsilyl ether (TBS-OR or TBDMS-OR), t-butyldiphenylsilyl ether (TBDPS-OR) diphenylmethylsilyl ether (DPM-OR) and the like. Non limiting examples of esters protecting groups are, for instance, trifluoroacetate, benzoate (Bz-OR) and carbonates, such as ethylcarbonate and the like, Non limiting examples of cyclic acetals or ketals protecting groups are, for instance, methylene acetal, ethylidene acetal, methoxymethylene acetal and the like.

The term "binding moiety" refers to a moiety that binds or associates the compound of formula (Ia) or (Ib) with the double strand of the DNA. The binding moiety can improve affinity properties of the derivatives to the DNA or improve alkylating reactivity of the alkylating agent or target different sequences of the DNA so as to modulate target specificity of the compound.

The term "self immolative group" refers to a chemical group able to form a bond with the oxygen atom of the thieno-indole scaffold, which becomes labile upon activation, leading to the rapid disassembly of the thieno-indole derivatives. Self-immolative systems are known to the person skilled in the art, see for example those described in WO2002/083180 and WO2004/043493, or those described in *Anticancer Agents in Medicinal Chemistry*, 2008, 8, 618-637 or in *Polym. Chem.* 2011, 2, 773-790.

The term "reactive moiety", refers to a chemical group able to react with a counterpart under relatively mild conditions and without the need of prior functionalization; said reaction will only require the application of some heat, pressure, a catalyst, acid, and/or base, Preferably, the reactive moiety is a group with an electrophilic function that reacts with nucleophiles, i.e. molecules that bear a nucleophilic group.

The term "nucleophilic group" refers to a species that donates an electron-pair to an electrophilic group to form a chemical bond in a chemical reaction. Examples of such nucleophilic groups include, but are not limited to, halogens, amines, nitrites, azides, alcohols, alkoxyde anions, carboxylate anions, thiols, thiolates, etc.

It is known to the person skilled in the art that transformation of a chemical functional group into another may require that one or more reactive centers in the compound containing such functional group have to be protected in order to avoid undesired side reactions. Protection of such reactive centers, and subsequent deprotection at the end of the synthetic transformations, can be accomplished following standard procedures described in the literature (see, for instance, Green, Theodora W. and Wuts, Peter G. M.—Protective Groups in Organic Synthesis, Third Edition, John Wiley & Sons Inc., New York (N.Y.), 1999).

Preferred compounds prepared with the process of the present invention are compounds of formula (Ia) as defined above.

More preferred are compounds of formula (Ia) wherein R1 is methyl, R2 is chlorine and BM, W1, Z1 and RM are as defined above.

More preferred are compounds of formula (Ia) wherein BM is a DNA binding moiety of formula (II-1) as defined above.

Most preferred specific compounds are the compounds of formula (Ia) listed below:

N-[6-(2,5-dioxo-2,5-dihydro-1H-pyrrol-1-yl)hexanoyl]-L-valyl-$N^5$-carbamoyl-N-[4-({[{3-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide (compd 1a);

N-[6-(2,5-dioxo-2,5-dihydro-1H-pyrrol-1-yl)hexanoyl]-L-valyl-$N^5$-carbamoyl-N-[4-({[{3-[({[(8S)-8-(chloromethyl)-1-methyl-6-({5-[(5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide (compd 2a);

N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (compd 3a);

N-[19-(2,5-dioxo-2,5-dihydro-1H-pyrrol-1-yl)-17-oxo-4,7,10,13-tetraoxa-16-azanonadecan-1-oyl]-L-valyl-$N^5$-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (compd 4a);

N-[19-(2,5-dioxo-2,5-dihydro-1H-pyrrol-1-yl)-17-oxo-4,7,10,13-tetraoxa-16-azanonadecan-1-oyl]-L-valyl-$N^5$-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7, 8-dihydro-6H-thieno[3,2-e]indol-4-yl]oxy}carbonyl)(methyl)amino]ethyl}(methyl)carbamoyl]oxy}methyl)phenyl]-L-ornithinamide (compd 5a) and N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (compd 6a).

As stated above, the present invention also provides an intermediate compound of formula (XIa) or (XIb):

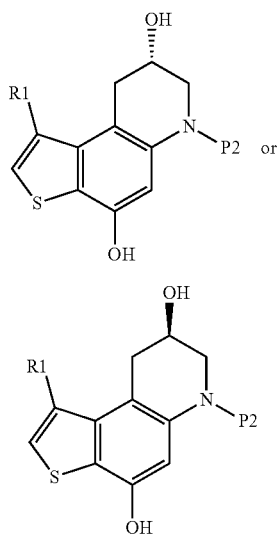

wherein R1 and P2 are as defined above.

Preferred intermediate compounds prepared with the process of the present invention are compounds of formula (XIa) or (XIb) wherein R1 is methyl and P2 is tert-butoxy carbonyl.

It is still another object of the present invention a process for preparing an intermediate compound of formula (XIa) or (XIb) as defined above, which process comprises the steps of a) N-alkylation of a compound of formula (VII) with an enantiopure compound of formula (VIIIa) or (VIIIb) to give respectively compounds of formula (IXa) or (IXb), using strong basic conditions;

b) intramolecular 6-endo-tet cyclization of the resulting compounds of formula (IXa) or (IXb)

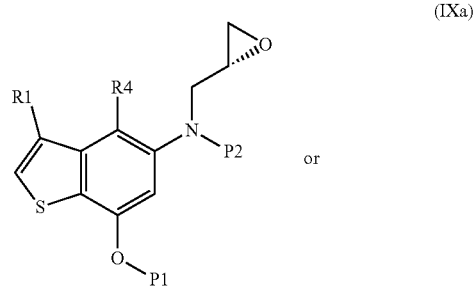

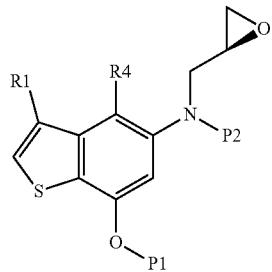

wherein R1, R4, P1 and P2 are as defined above, with metallo-organic reagents and c) selective removal of the hydroxyl protecting group P1, as defined above.

According to step a), the coupling of the 5-amino-4-halo-3-alkyl-1-benzothiophen-7-ol of formula (VII) with (S)-glycidyl 3-nosylate (VIIIa) or (R) glycidyl 3-nosylate (VIIIb) to give a compound of formula (IXa) or (IXb) respectively, is performed using strong basic conditions, such as, for example, n-buthyllithium, t-BuOK, or preferably NaH. Preferably, the reaction is carried out at a temperature ranging from −10° C. to 50° C. in an organic solvent such as, for example, THF, Et$_2$O, DMA, DMF, or a mixture thereof.

According to step b), conversion of a compound of formula (IXa) or (IXb) into a compound of formula (Xa) or (Xb), respectively, is carried out using a Grignard reagent, as for example i-PrMgCl.LiCl, s-Bu$_2$MgLi.Cl, MeMgBr, i-PrMgBr or preferably, EtMgBr. Preferably, the reaction is carried out at a temperature ranging from −5° C. to 50° C. in an organic solvent such as, for example, THF, Et$_2$O, DCM, or a mixture thereof.

According to step c), removal of the hydroxyl protecting group from compound of formula (Xa) or (Xb), to yield compound of formula (XIa) or (XIb), respectively, is carried out by known procedures as for example those reported in Protective Groups in Organic Synthesis; Theodora W. Green, Peter G. M. Wuts. Particularly, when a benzyl protecting group has to be removed, the reaction is carried out by catalytic hydrogenation conditions with a hydrogenation catalyst, preferably 10% Pd/C, and a hydrogen source, preferably HCO$_2$NH$_4$. Preferably, the reaction is carried out at a temperature ranging from 0° C. to reflux in an organic solvent such as, for example, THF, Et$_2$O, DCM, Mead, EtOH or a mixture thereof.

According to step d), internal spirocyclization to convert a compound of formula (XIa) or (XIb) to a compound of formula (XIIa) or (XIIb), respectively, is promoted by Mitsunobu activation of the secondary alcohol with organophosphorus(III) compounds, preferably phosphines such as e.g. Ph$_3$P, Bu$_3$P and in presence of azoderivative compounds, preferably diisopropyl azodicarboxylate (DAED) or 1,1'-(azodicarbonyl)-dipiperidine (ADDP). Preferably, the reaction is carried out at a temperature ranging from −10° C. to 50° C. in an organic solvent such as, for example, THF, Et$_2$O, DCM, or a mixture thereof.

According to step e), stereocontrolled regioselective opening of the cyclopropane ring of compound of formula (XIIa) or (XIIb) to yield a compound of formula (XIIIa) or (XIIIb), respectively, is carried out under controlled acidic conditions, preferably with HCl. Preferably, the reaction is carried out at a temperature ranging from −80° C. to 25° C. in an organic solvent such as, for example, ETOAc, Et$_2$O, DCM, or a mixture thereof.

According to step f), removal of the amino protecting group from a compound of formula (XIIIa) or (XIIIb) to yield a compound of formula (XIVa) or (XIVb), respectively, is carried out by known procedures as for example those reported in Protective Groups in Organic Synthesis; Theodora W. Green, Peter G. M. Wuts. Particularly, when t-buthoxycarbonyl protecting group has to be removed, the reaction is carried out under acidic conditions with TFA, or preferably HCl. Preferably, the reaction is carried out at a temperature ranging from 0° C. to reflux in an organic solvent such as, for example, EtOAc, DCM, MeOH, or a mixture thereof.

According to step g) the coupling reaction of the intermediate (XIVa) or (XIVb) with the BM-COCH residue to yield a compound of formula (XVa) or (XVb) is carried out in presence of a condensing agent, such as, for example, DCC, EDC, or preferably EDCl. The reaction is carried out at a temperature ranging from 0° C. to 100° C. in an organic solvent such as, for example, DMF.

According the steps h) and i), the derivatization of the key enantiopure intermediate of formula (XVa) or (XVb) to yield a compound of formula (Ia) or (Ib) is carried out following the procedures reported in the prior art references, such as those reported in step e''') at page 63 of WO2013/149948.

EXPERIMENTAL SECTION

In the examples below, as well as throughout the application, the following abbreviations have the following meanings. If not defined, the terms have their generally accepted meanings.

| ABBREVIATIONS | |
|---|---|
| ACN | Acetonitrile |
| AcOH | Acetic Acid |
| ee | Enantiomeric excess |
| EtOAc | Ethyl acetate |
| DCM | Dichloromethane |
| DMA | N,N-dimethylacetamide |
| DMF | N,N-dimethylformamide |
| DMSO | Dimethyl sulfoxide |
| Et$_2$O | Diethyl ether |
| EtOH | Ethanol |
| HCl | Hydrochloric acid |
| MeOH | Methanol |
| NaH | Sodium Hydride |
| NH$_4$OAc | Ammonium Acetate |
| NaHCO$_3$ | Sodium hydrogencarbonate |
| TEA | Triethylamine |
| TFA | Trifluoroacetic acid |
| THF | Tetrahydrofurane |
| t-BuOK | Potassium tert-butoxide |
| NH$_4$OH | Ammonium hydroxide |
| NaCl | Sodium chloride |
| g | Gram |
| Kg | Kilogram |
| mL | Milliliter |
| L | Liter |
| M | Molar |
| N | Normal |
| h | Hour/s |
| min | Minute/s |
| Hz | Hertz |
| MHz | Mega-Hertz |

| ABBREVIATIONS | |
|---|---|
| ESI | Electrospray ionization |
| HPLC | High-performance liquid chromatography |
| TLC | Thin-layer chromatography |

$^1$H-NMR spectra were recorded at a constant temperature of 25° C. on a Varian INOVA 500 spectrometer, operating at 499.7 MHz and equipped with a 5 mm Triple Resonance Indirect detection Probe ($^1$H{$^{13}$C, $^{15}$N}).

Chemical shifts were referenced with respect to the residual solvent signal, DMSO-d$_6$ at 2.50 ppm, for $^1$H. Data are reported as follows: chemical shift, multiplicity (s=singlet, d=doublet, t=triplet, q=quartet, bs=broad singlet, dd=doublet of doublet, td=triplet of doublet, m=multiplet), coupling constants, and number of protons. HPLC-MS/UV analyses were performed on a LCQ DecaXP (Thermo, San Jose, US) ion trap instrument, equipped with an electrospray (ESI) ion source. The mass spectrometer is connected to a Surveyor HPLC system (Thermo, San Jose, US) with an UV photodiode array detector (UV detection 215-400 nm). A Waters XSelect CSH C18 column 50×4.6 mm, 3.5 μm particle size was used. Mobile phase A was ammonium acetate 5 mM buffer (pH 4.5 with acetic acid):acetonitrile 95:5, and mobile phase B was ammonium acetate 5 mM buffer (pH 4.5 with acetic acid):acetonitrile 5:95. Gradient from 0 to 100% B in 7 minutes, hold 100% B 2 minutes. Flow rate mL/min. Injection volume 10 μL. Retention times (R$_t$) are given in minutes. Full scan, mass range from 100 to 1200 amu. Heated capillary temp was 275° C. and Spray voltage value was set at 4 kV. Mass are given as m/z ratio.

Instrument control, data acquisition and processing were performed by using Xcalibur 1.2 software (Thermo).

High resolution mass spectra (HRMS) were obtained on a TOF Waters LCT Premier XE mass detector with ESI interface. The assay was based on generic gradient reversed phase chromatography carried out on a Waters Alliance liquid chromatograph mod. 2795. The eluent from the HPLC column was split and 25 μL/min were mixed with a 100 μL/min stream of a 30/10/60 (v/v/v) mixture of MeOH/iPrOH/H$_2$O containing 0.01% w/v of formic acid and 80 nM Trimethoprim coming from a Waters Reagent Manager pump before entering the MS source. The ESI source was operated at 100° C., 2.5 kV capillary voltage, 60 V cone, 600 L/hr nitrogen desolvation flow at 350° C. and 10 L/h nitrogen cone flow. Trimethoprim was chosen as stable, soluble and appropriate reference compound for real-time single-point mass correction. ES(+) full scan 80 1200 amu centroided data acquisition was carried out at 2 Hz sampling rate in the "W" mode. The LCT embedded PC provided both real time data centroiding and real time mass correction based on the Trimethoprim.H+ reference mass of 291.1452 Da. Proper intensity MS spectra (40 to 2000 analyte counts) were averaged to obtain the final result.

The enantiomeric excess (% ee) of the compounds was determined by Chiral HPLC resolution of the enantiomeric mixture using the following conditions: Temperature: 25° C.; Flow rate: 0.7 mL/min; Column: CHIRACEL OD 4.6× 250 mm, 20 μm; Injection volume: 20 μL; Mobile phase A: Hexane; Mobile phase B: EtOH; Isocratic condition 55% of B.

Example 1

Synthesis of N-[6-(2,5-dioxo-2,5-dihydro-1H-pyrrol-1-yl)hexanoyl]-L-valyl-N⁵-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 6a)

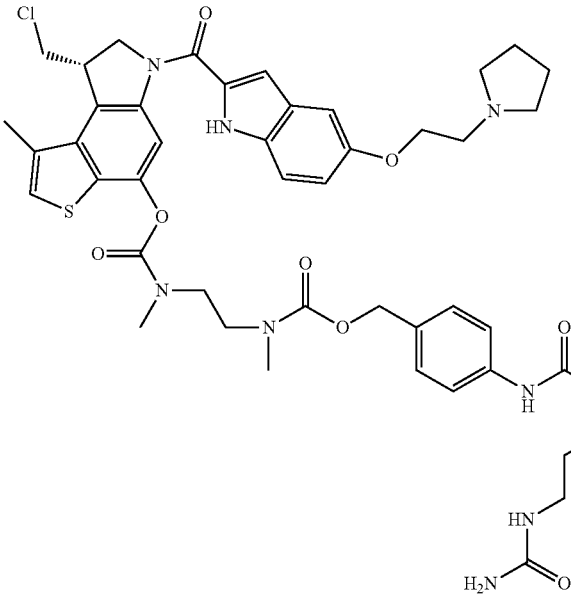

A solution of tert-butyl [7-(benzyloxy)-4-iodo-3-methyl-1-benzothiophen-5-yl]carbamate (VII') prepared as reported in GB2344818 (515 mg, 1.04 mmol) and commercially available (S)-glycidyl 3-nosylate (337 mg, 1.3 mmol) in dry DMF (12 mL) was cooled to 0° C. and treated with NaH (60% dispersion in mineral oil, 61 mg, 1.56 mmol). The resulting solution was stirred at 0° C. for 5 h, then poured into ice-cold water and extracted with ethyl acetate (200 mL). The organic layer was washed with water (100 mL), with saturated aqueous NaCl (100 mL), dried over Na₂SO₄, filtered and concentrated. The residue was purified by flash chromatography (6-12% EtOAc/n-hexane gradient elution) to provide the title intermediate (500 mg, 87%) as a white solid.

¹H NMR (DMSO-d₆,500 MHz): δ=7.59 (br. s., 1H), 7.44-7.52 (m, 2H), 7.30-7.43 (m, 3H), 7.00-7.17 (m, 1H), 5.25-5.39 (m, 2H), 3.87-3.97 (m, 1H), 3.06-3.27 (m, 2H), 2.68 (s, 3H), 2.57-2.67 (m, 1H), 2.25-2.47 (m, 1H), 1.16-1.57 (m, 9H)

HPLC-MS (ESI)/UV (215-400 nm); [M+H]⁺ 552; R_t 8.43 min.

Step a)

Preparation of the Intermediate tert-butyl [7-(benzyloxy)-4-iodo-3-methyl-1-benzothiophen-5-yl][(2S)-oxiran-2-ylmethyl]carbamate (IXa')

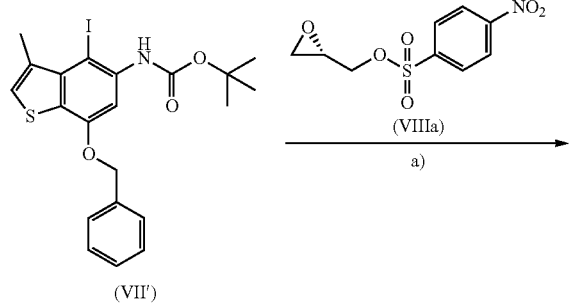

Step b)

Preparation of the Intermediate tert-butyl (8S)-4-(benzyloxy)-8-hydroxy-1-methyl-8,9-dihydrothieno[3,2-f]quinoline-6(7H)-carboxylate (Xa')

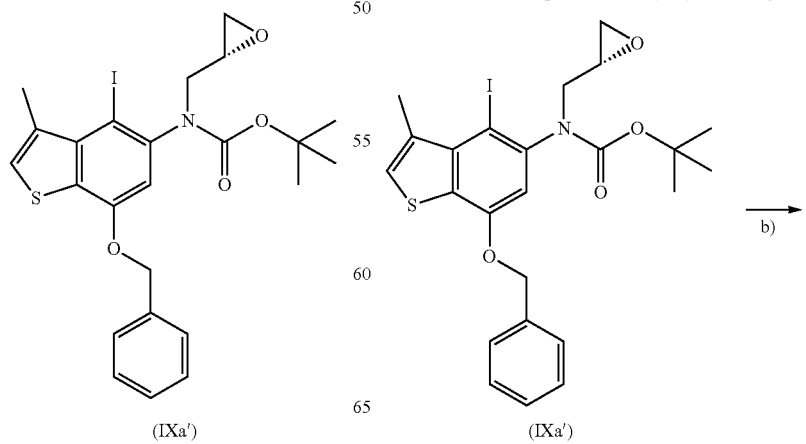

-continued

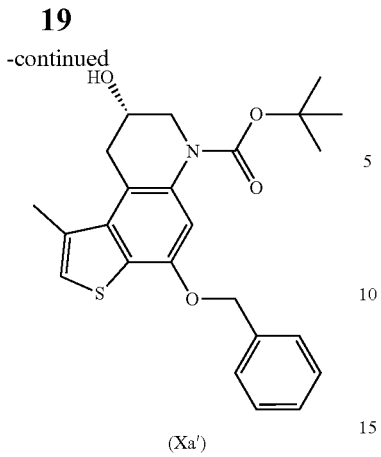

(Xa')

A solution of intermediate (IXa') from step a) (360 mg, 0.661 mmol) in dry THF (4 mL) was treated with EtMgBr (1.3 mL, 1.0 M in THF) at 0° C. under nitrogen atmosphere. The reaction mixture was stirred at room temperature for 1 h, quenched with the addition of saturated aqueous NH$_4$Cl and extracted twice with EtOAc (2×40 mL). An aqueous solution of p-toluenesulfonic acid monohydrate (2 g in 4 mL of water) was added to the combined organic layers, and the reaction mixture was stirred for 15 minutes. The reaction was quenched by addition of a 1 M aqueous Na$_2$CO$_3$ solution. Layers were separated and the organic layer was washed with saturated aqueous NaCl and dried over Na$_2$SO$_4$. The solvent was removed under reduced pressure and the residue was purified by flash chromatography (20-40% diethyl ether/n-hexane gradient elution) to provide the title intermediate (Xa') as a white solid (185 mg, 65%).

$^1$H NMR (DMSO-d$_6$, 500 MHz): δ=7.45-7.52 (m, 2H), 7.41 (t, J=7.4 Hz, 2H), 7.33-7.37 (m, J=7.3 Hz, 1H), 7.31 (s, 1H), 7.06 (s, 1H), 5.19-5.27 (m, 2H), 5.18 (d, J=4.0 Hz, 1H), 3.98 (m, 1H), 3.82 (dd, J=12.4, 3.2 Hz, 1H), 3.54 (dd, J=16.7, 6.1 Hz, 1H), 3.29 (dd, J=12.4, 7.8 Hz, 1H), 3.03 (dd, J=16.7, 6.4 Hz, 1H), 2.58 (s, 3H), 1.43 (s, 9H)

HPLC-MS (ESI)/UV (215-400 nm): [M+H]$^+$ 426; R$_t$ 7.50 min

Step c)

Preparation of the Intermediate tert-butyl (8S)-4,8-dihydroxy-1-methyl-8,9-dihydrothieno[3,2-f]quinoline-6(7H)-carboxylate (XIa')

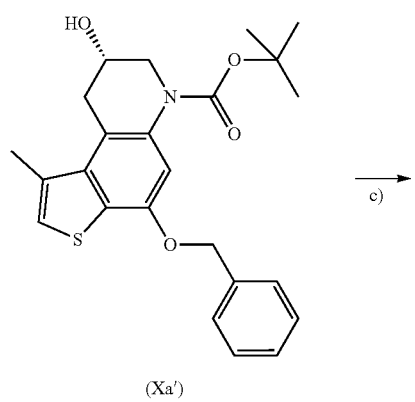

(Xa')

-continued

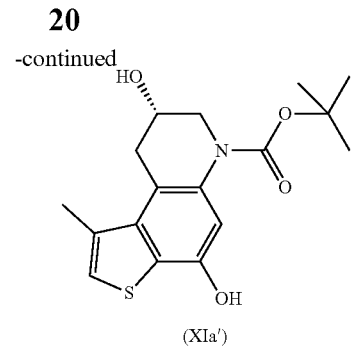

(XIa')

A solution of intermediate (Xa') from step b) (148 mg, 0.347 mmol) in THF (30 mL) was treated with 10% Pd/C (70 mg) and 25% aqueous solution of HCO$_2$NH$_4$ (2 mL) and stirred for 2 hours. The mixture was filtered through a pad of Celite, the solvent was removed under reduced pressure and the residue was purified by flash chromatography (30% diethyl ether/toluene elution) to provide the title intermediate (XIa') as a white solid (90 mg, 80%).

$^1$H NMR (DMSO-d$_6$, 500 MHz): δ=10.07 (s, 1H), 7.24 (s, 1H), 6.92 (s, 1H), 5.14 (d, J=4.0 Hz, 1H), 3.95 (m, 1H), 3.80 (dd, J=12.4, 3.4 Hz, 1H), 3.51 (dd, J=16.5, 6.1 Hz, 1H), 3.27 (dd, J=12.4, 7.8 Hz, 1H), 2.99 (dd, J=16.5, 6.6 Hz, 1H), 2.56 (s, 3H), 1.46 (s, 9H)

HPLC-MS (ESI)/UV (215-400 nm): [M+H]$^+$ 336; R$_t$ 5.59 min

Step d)

Preparation of the Intermediate tert-butyl (7aS,8aR)-4-hydroxy-1-methyl-7,7a,8,8a-tetrahydro-6H-cyclopropa[c]thieno[3,2-f]quinoline-6-carboxylate (XIIa')

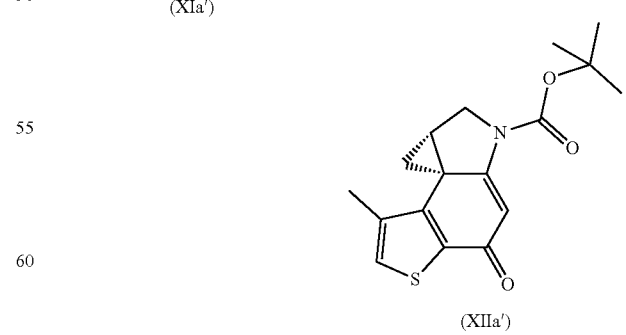

A solution of intermediate (XIa') from step c) (60 mg, 0.178 mmol) in dry THF (15 mL) was treated, under nitrogen atmosphere, with tributylphosphine (0.258 mL, 0.89 mmol) and 1,1'-(azodicarbonyl)-dipiperidine (ADDP, 225 mg, 0.89 mmol). The reaction mixture was stirred for 1 h at room temperature, quenched with the addition of water and extracted with diethyl ether. The organic layer was washed with water and saturated aqueous NaCl, dried over Na$_2$SO$_4$, and concentrated. The residue was purified by flash chromatography (50% diethyl ether/n-hexane elution) to yield the title intermediate (XIIa') as a white solid (48 mg, 85%).

$^1$H NMR (DMSO-d$_6$, 500 MHz): δ=7.54 (d, J=0.9 Hz, 2H), 6.57 (br. s., 1H), 3.90-4.00 (m, 2H), 3.37 (m, 1H), 2.16 (d, J=0.9 Hz, 3H), 2.13 (dd, J=7.7, 4.5 Hz, 1H), 1.50 (s, 9H), 1.37 (t, J=4.9 Hz, 2H)

HPLC-MS (ESI)/UV (215-400 nm): [M+H]$^+$ 318; R$_t$ 6.06 min

Steps e-f)

Preparation of the key intermediate (8S)-8-(chloromethyl)-1-methyl-7,8-dihydro-6H-thieno[3,2-e]indol-4-ol (XIVa')

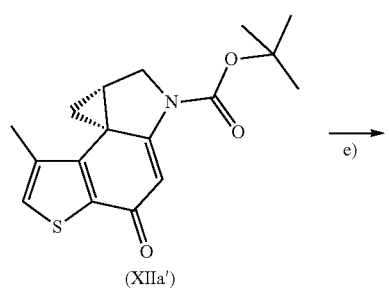

(XIIa')

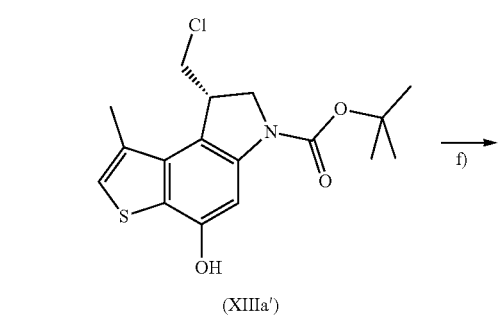

(XIIIa')

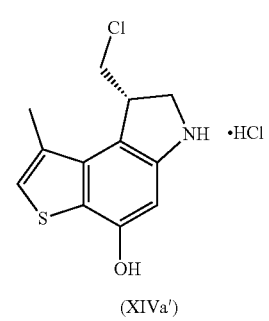

(XIVa')

A solution of intermediate (XIIa') from step d) (22 mg, 0.0693 mmol) in EtOAc (1 mL) at −78° C. was treated with 3.5 N HCl in EtOAc (2.0 mL) and stirred at −78° C. for 45 minutes. The solution was warmed to room temperature and stirred for 2 h. The solvent and HCl gas were removed under a stream of nitrogen and the residue was dried under vacuum to yield the title intermediate (XIVa') (18 mg, 90%) that was used without further purification in the next step.

Step g)

Preparation of the Key Intermediate [(8S)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl}methanone hydrochloride (XVa')

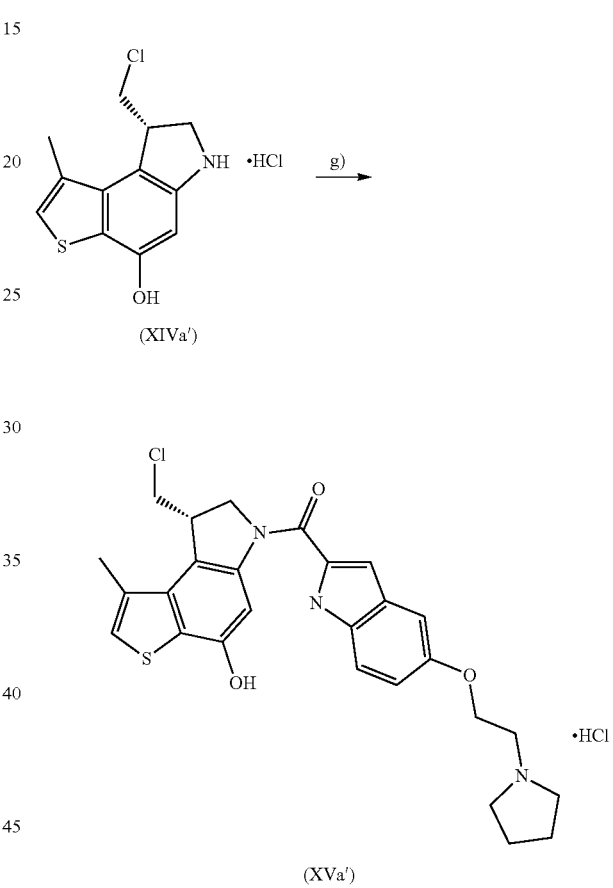

Crude intermediate (XIVa') from step e) was dissolved in DMF dry (3.5 mL) and EDCl (53 mg, 0.277 mmol) and 5-[2-(pyrrolidin-1-yl)ethoxy]-1H-indole-2-carboxylic acid (1.7 eq.) were added. The resulting reaction mixture was stirred overnight under nitrogen atmosphere. After adding 300 mg silica gel, the solvent was removed under reduced pressure and the residue was purified in flash chromatography (DCM/MeOH/HCl in dioxane=100/8/0.2 elution) to provide intermediate of formula (XVa') (32 mg, 84%) as a white solid.

HPLC-MS (ESI)/UV (215-400 nm): [M+H]$^+$ 510; R$_t$ 5.98 min

Chiral HPLC, rt=10.68; ee>99%.

$^1$H NMR (DMSO-d$_5$, 500 MHz): δ=11.69 (s, 1H), 10.54 (s, 1H), 10.03 (br. s., 1H), 7.85 (br. s., 1H), 7.41-7.46 (m, 2H), 7.26 (s, 1H), 7.08 (d, J=1.5 Hz, 1H), 7.00 (dd, J=8.9, 2.2 Hz, 1H), 4.67 (dd, J=10.7, 8.1 Hz 1H), 4.56 (d, J=10.7

Hz, 1H), 4.31 (br. s., 2H), 4.17 (td, J=8.4, 2.3 Hz, 1H), 3.89 (dd, J=11.1, 2.7 Hz, 1H), 3.59 (m, 4H), 3.14 (m, 2H), 2.54 (d, J=0.9 Hz, 3H), 1.92 (br.s, 4H)

Steps h), i)

Synthesis of the Final Thermo-Indole Title Compound (compd 6a)

Starting from the key enantiopure intermediate (XVa') obtained as described in the preparations above from Step a) to Step g) and operating as described in WO2013/149948 on page 63 the title compound N-[6-(2,5-dioxo-2,5-dihydro-1H-pyrrol-1-yl)hexanoyl]-L-valyl-$N^5$-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 6a) was obtained.

ESI MS: m/z 1222 (MH+)

$^1$H NMR (400 MHz, dmf-d7) δ ppm 0.95 (t, J=7.8 Hz, 6H) 2.16 (m, 1H) 2.66 (br. s., 3H) 2.99-3.09 (m, 3H) 3.09-3.29 (m, 3H) 3.59 (br. s., 2H) 3.69 (br, s., 2H) 3.81 (br. s., 2H) 4.04 (d, J=10.7 Hz, 1H) 4.31-4.47 (m, 2H) 4.61 (br. s., H) 4.83 (br. s., 2H) 5.11 (d, J=15.7 Hz, 2H) 5.60 (s, 2H) 6.29 (br. s., 1H) 7.00 (m, 3H) 7.30 (m, 2H) 7.53 (d, J=8.5 Hz, 2H) 7.88 (d, J=8.2 Hz, 1H) 8.13 (d, J=7.8 Hz, 1H) 8.27 (s, 1H) 10.1 (m, 1H) 11.61 (br.s., 1H)

Example 2

Synthesis of N-[6-(2,5-dioxo-2,5-dihydro-1H-pyrrol-1-yl)hexanoyl]-L-valyl-$N^5$-carbamoyl-N-[4-({[{2-[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 6b)

By the procedure analogous to Example 1 and starting from commercially available (R)-glycidyl 3-nosylate, the following intermediates were prepared:

tert-butyl [7-(benzyloxy)-4-iodo-3-methyl-1-benzothiophen-5-yl][(2R)-oxiran-2-ylmethyl]carbamate (IXb', Step a)

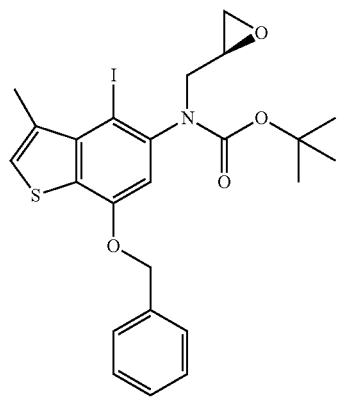

$^1$H NMR (DMSO-d$_6$, 500 MHz): δ=7.59 (br. s., 1H), 7.44-7.52 (m, 2H), 7.30-7.43 (m, 3H), 7.00-7.17 (m, 1H), 5.25-5.39 (m, 2H), 3.87-3.97 (m, 1H), 3.06-3.27 (m, 2H), 2.68 (s, 3H), 2.57-2.67 (m, 1H), 2.25-2.47 (m, 1H), 1.16-1.57 (m, 9H)

HPLC-MS (ESI)/UV (215-400 nm): [M+H]$^+$ 552; R$_t$ 8.43 min.

tert-butyl (8R)-4-(benzyloxy)-8-hydroxy-1-methyl-8,9-dihydrothieno[3,2-f]quinoline-6(7H)-carboxylate (Xb', Step b)

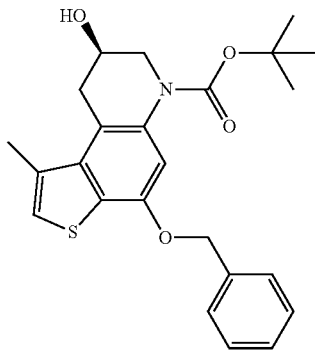

$^1$H NMR (DMSO-d$_6$, 500 MHz): δ=7.45-7.52 (m, 2H), 7.41 (t, J=7.4 Hz, 2H), 7.33-7.37 (m, J=7.3 Hz, 1H), 7.31 (s, 1H), 7.06 (s, 1H), 5.19-5.27 (m, 2H), 5.18 (d, J=4.0 Hz, 1H), 3.98 (m, 1H), 3.82 (dd, J=12.4, 3.2 Hz, 1H), 3.54 (dd, J=16.7, 6.1 Hz, 1H), 3.29 (dd, J=12.4, 7.8 Hz, 1H), 3.03 (dd, J=16.7, 6.4 Hz, 1H), 2.58 (s, 3H), 1.43 (s, 9H)

HPLC-MS (ESI)/UV (215-400 nm): [M+H]$^+$426; R$_t$ 7.50 min tert-butyl (8R)-4,8-dihydroxy-1-methyl-8,9-dihydrothieno[3,2-f]quinoline-6(7H)-carboxylate (XIb', Step c)

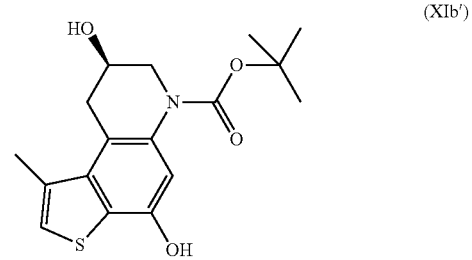 [SMILES: Cc1csc2c(O)cc3c(c12)C[C@@H](O)CN3C(=O)OC(C)(C)C]

NMR (DMSO-d$_6$, 500 MHz): δ=10.07 (s, 1H), 7.24 (s, 1H), 6.92 (s, 1H), 5.14 (d, J=4.0 Hz, 1H), 3.95 (m, 1H), 3.80 (dd, J=12.4, 3.4 Hz, 1H), 3.51 (dd, J=16.5, 6.1 Hz, 1H), 3.27 (dd, J=12.4, 7.8 Hz, 1H), 2.99 (dd, J=16.5, 6.6 Hz, 1H), 2.56 (s, 3H), 1.46 (s, 9H)

HPLC-MS (ESI)/UV (215-400 nm): [M+H]$^+$ 336; R$_t$ 5.59 min tert-butyl (7aR,8aS)-4-hydroxy-1-methyl-7,7a,8,8a-tetrahydro-6H-cyclopropa[c]thieno[3,2-f]quinoline-6-carboxylate (XIIb', Step d)

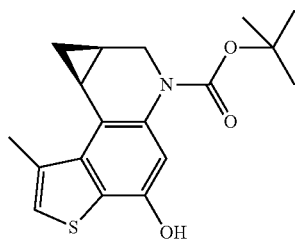

(XIIb')

$^1$H NMR (DMSO-d$_6$, 500 MHz): δ=7.54 (d, J=0.9 Hz, 2H), 6.57 (br. s., 1H), 3.90-4.00 (m, 2H), 3.37 (m, 1H), 2.16 (d, J=0.9 Hz, 3H), 2.13 (dd, J=7.7, 4.5 Hz, 1H), 1.50 (s, 9H), 1.37 (t, J=4.9H, 2H)

HPLC-MS (ESI)/UV (215-400 nm); [M+H]$^+$ 318; R$_t$ 6.06 min (8R)-8-(chloromethyl)-1-methyl-7,8-dihydro-6H-thieno[3,2-e]indol-4-ol (XIVb', Steps e-f)

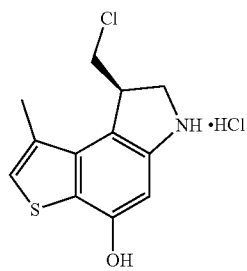

(XIVb')

[(8R)-8-(chloromethyl)-4-hydroxy-1-methyl-7,8-dihydro-6H-thieno[3,2-e]indol-6-yl]{5-[2-(pyrrolidin-1-yl)ethoxy]-1H-indol-2-yl}methanone hydrochloride (XVb', Step g)

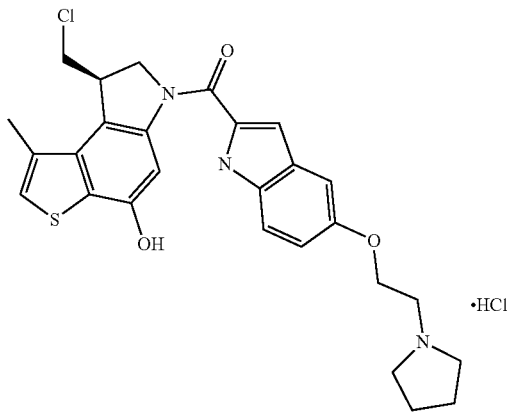

(XVb')

Chiral HPLC, rt=13.20; ee>99%.

$^1$H NMR (DMSO-d$_6$, 500 MHz): δ=11.69 (s, 1H), 10.54 (s, 1H), 10.03 (br, s., 1H), 7.85 (br. s., 1H), 7.41-7.46 (m, 2H), 7.26 (s, 1H), 7.08 (d, J=1.5 Hz, 1H), 7.00 (dd, J=8.9, 2.2 Hz, 1H), 4.67 (dd, J=10.7, 8.1 Hz 1H), 4.56 (d, J=10.7 Hz, 1H), 4.31 (br. s., 2H), 4.17 (td, J=8.4, 2.3 Hz, 1H), 3.89 (dd, J=11.1, 2.7 Hz, 1H), 3.59 (m, 4H), 3.14 (m, 2H), 2.54 (d, J=0.9 Hz, 3H), 1.92 (br.s, 4H)

Synthesis of the Final Thieno-Indole Title Compound: N-[6-(2,5-dioxo-2,5-dihydro-1H-pyrrol-1-yl)hexanoyl]-L-valyl-N$^5$-carbamoyl-N-[4-({[{2-[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (compd 6b) (Steps h, i)

Starting from the key enantiopure intermediate (XVb') obtained as described in the preparations and operating as described in WO2013/149948 on page 63 the corresponding enantiopure title N-[6-(2,5-dioxo-2,5-dihydro-1H-pyrrol-1-yl)hexanoyl]-L-valyl-N$^5$-carbamoyl-N-[4-({[{2-[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 6b) was obtained

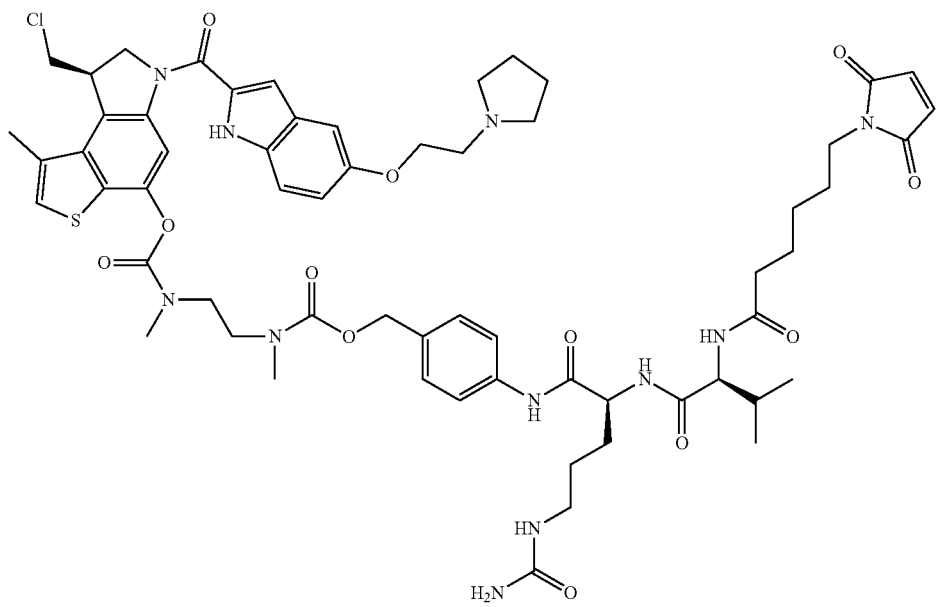 [SMILES: Cc1csc2c(OC(=O)N(C)CCN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@@H](CCl)CN3C(=O)c1cc2cc(OCCN3CCCC3)ccc2[nH]1]

ESI MS: m/z 1222 (MH+)

$^1$H NMR (400 MHz, dmf-d7) δ ppm 0.95 (t, J=7.8 Hz, 6H) 2.16 (m, 1H) 2.66 (br. s., 3H) 2.99-3.09 (m, 3H) 3.09-3.29 (m, 3H) 3.59 (br. s., 2H) 3.69 (br, s., 2H) 3.81 (br. s., 2H) 4.04 (d, J=10.7 Hz, 1H) 4.31-4.47 (m, 2H) 4,61 (br. s., 1H) 4.83 (br, s., 2H) 5.11 (d, J=15.7 Hz, 2H) 5.60 (s, 2H) 6.29 (br, s., 1H) 7.00 (m, 3H) 7.30 (m, 2H) 7.53 (d, J=8.5 Hz, 2H) 7.88 (d, J=8.2 Hz, 1H) 8.13 (d, J=7.8 Hz, 1H) 8.27 (s, 1H) 10.1 (m, 1H) 11.61 (br.s., 1H)

Example 3

Starting from different key intermediates of formula (XIVa) or (XIVb) and following the procedures described in the Examples 1 and 2 above and in WO2013/149948 from page 43 to page 79 the following compounds were prepared:

N-[6-(2,5-dioxo-2,5-dihydro-1H-pyrrol-1-yl)hexanoyl]-L-valyl-N$^5$-carbamoyl-N-[4-({[{3-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-ornithinamide (compd. 1a)

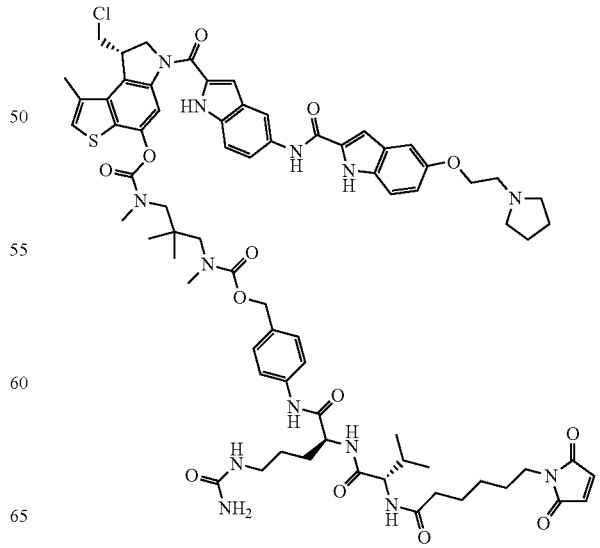

29

N-[6-(2,5-dioxo-2,5-dihydro-1H-pyrrol-1yl)hexanoyl]-L-valyl-N⁵-carbamoyl-N-[4-({[{3-[({[(8S)-8-(chloromethyl)-1-methyl-6-({5-[2-(pyrrolidin-1yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide (Compd 2a)

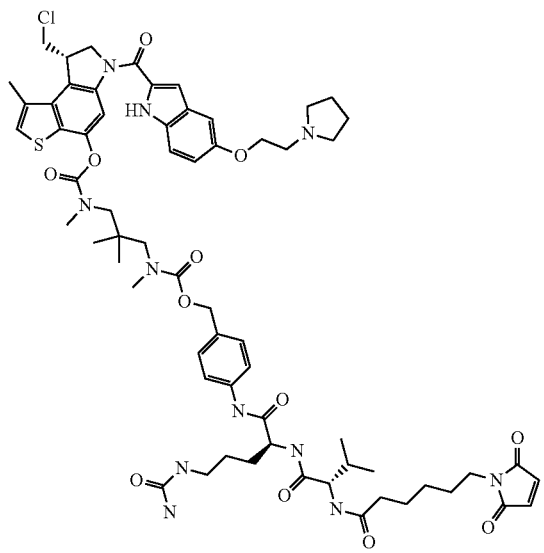 [SMILES: Cc1csc2c(OC(=O)N(C)CC(C)(C)CN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@H](CCl)CN3C(=O)c1cc2cc(OCCN3CCCC3)ccc2[nH]1]

N-[6-(2,5-dioxo-2,5-dihydro-1H-pyrrol-1-yl)hexanoyl]-L-valyl-N⁵-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 3a)

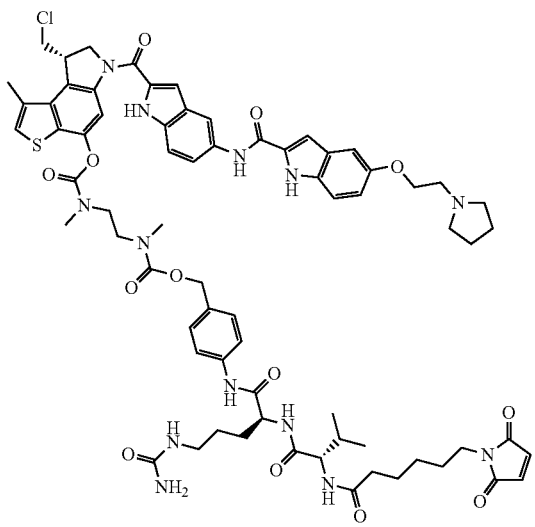 [SMILES: Cc1csc2c(OC(=O)N(C)CCN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@H](CCl)CN3C(=O)c1cc2cc(NC(=O)c3cc4cc(OCCN5CCCC5)ccc4[nH]3)ccc2[nH]1]

30

N-[19-(2,5-dioxo-2,5-dihydro-1H-pyrrol-1-yl)-17-oxo-4,7,10,13-tetraoxa-16-azanonadecan-1-oyl]-L-valyl-N⁵-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 4a)

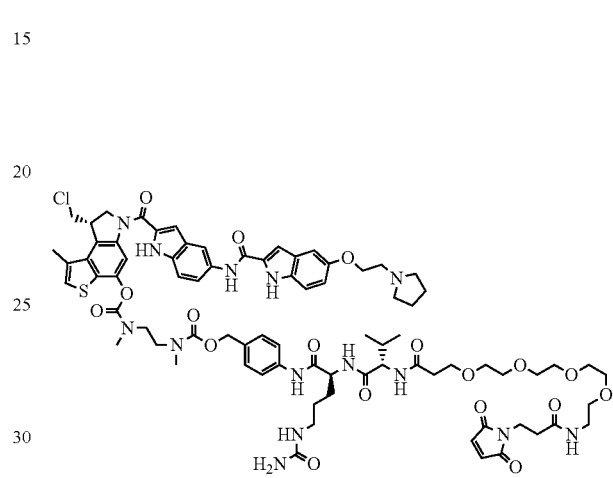

N-[19-(2,5-dioxo-2,5-dihydro-1H-pyrrol-1-yl)-17-oxo-4,7,10,13-tetraoxa-16-azanonadecan-1-oyl]-L-valyl-N⁵-carbamoyl-N-[4-({[{2-[({[(8S)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 5a)

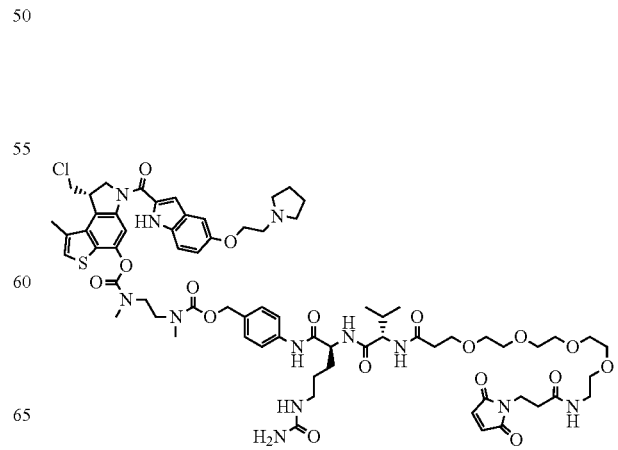

31

N-[6-(2,5-dioxo-2,5-dihydro-1H-pyrrol-1-yl)hexanoyl]-L-valyl-$N^5$-carbamoyl-N-[4-({[{3-[({[(8R)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide (compd 1b)

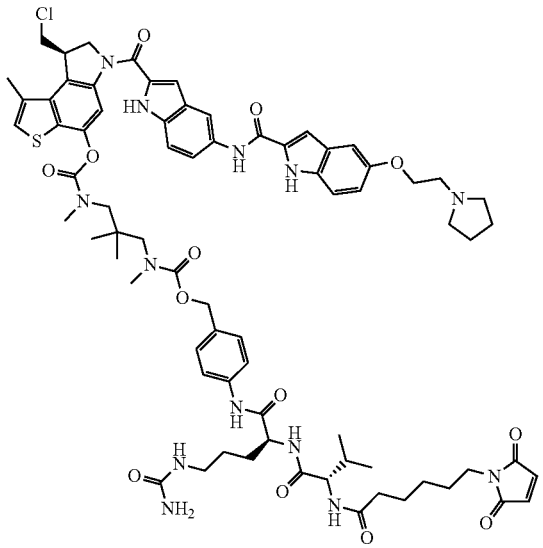 [SMILES: Cc1csc2c(OC(=O)N(C)CC(C)(C)CN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@@H](CCl)CN3C(=O)c1cc2cc(NC(=O)c3cc4cc(OCCN5CCCC5)ccc4[nH]3)ccc2[nH]1]

N-[6-(2,5-dioxo-2,5-dihydro-1H-pyrrol-1yl)hexanoyl]-L-valyl-$N^5$-carbamoyl-N-[4-({[{3-[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amino]-2,2-dimethylpropyl}(methyl)carbamoyl]oxy}methyl)phenyl]-L-ornithinamide (Compd 2b)

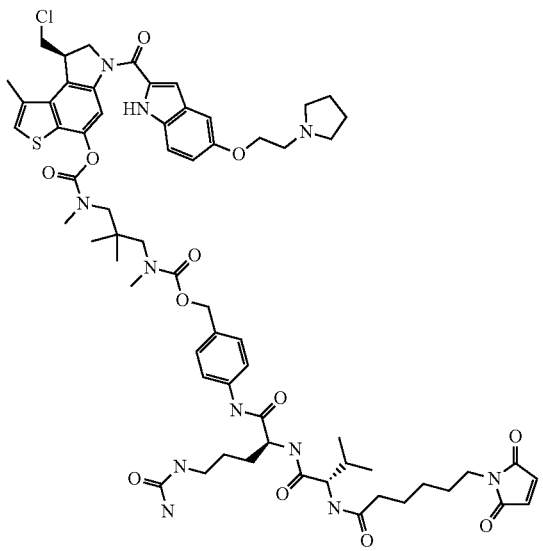 [SMILES: Cc1csc2c(OC(=O)N(C)CC(C)(C)CN(C)C(=O)OCc3ccc(NC(=O)[C@H](CCCNC(N)=O)NC(=O)[C@@H](NC(=O)CCCCCN4C(=O)C=CC4=O)C(C)C)cc3)cc3c(c12)[C@@H](CCl)CN3C(=O)c1cc2cc(OCCN3CCCC3)ccc2[nH]1]

32

N-[6-(2,5-dioxo-2,5-dihydro-1H-pyrrol-1yl)hexanoyl]-L-valyl-$N^5$-carbamoyl-N-[4-({[{2-[({[(8R)-8-(chloromethyl)-1-methyl-6-({5-[({5-[2-(pyrrolidin-1-yl)ethoxy]-1H-indol-2-yl}carbonyl)amino]-1H-indol-2-yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 3b)

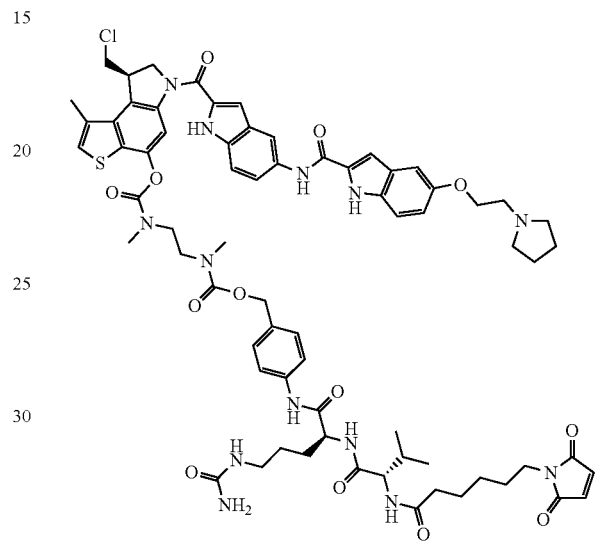

N-[19-(2,5-dioxo-2,5-dihydro-1H-pyrrol-1-yl)-17-oxo-4,7,10,13-tetraoxa-16-azanonadecan-1-oyl]-L-valyl-$N^5$-carbamoyl-N-[4-({[{2-[({[(8S)-8-(chloromethyl)-1-methyl-6-({5-[({5-[2-(pyrrolidin-1-yl)ethoxy]-1H-indol-2-yl}carbonyl)amino]-1H-indol-2yl}carbonyl)-7,8-dihydro-6H-thieno[3,2-e]indol-4-yl]oxy}carbonyl)(methyl)amino]ethyl}(methyl)carbamoyl]oxy}methyl)phenyl]-L-ornithinamide (Compd 4b)

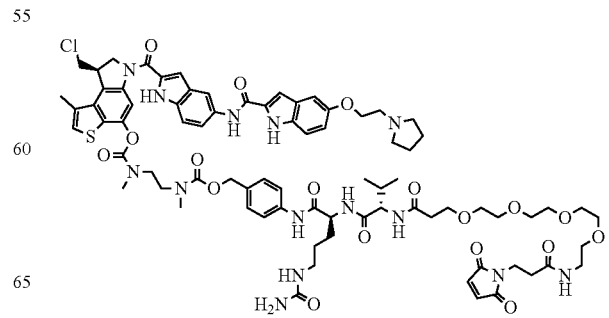

N-[19-(2,5-dioxo-2,5-dihydro-1H-pyrrol-1yl)-17-oxo-4,7,10,13-tetraoxa-16-azanonadecan-1-oyl]-L-valyl-N⁵-carbamoyl-N-[4-({[{2-[({[(8R)-8-(chloromethyl)-1-methyl-6-({5-[2-(pyrrolidin-1-yl)ethoxy]-1H-indol-2-yl}carbonyl)-7,8-dihydro-6H-thieno[3,2-e]indol-4-yl]oxy}carbonyl)(methyl)amine]ethyl}(methyl)carbamoyl]oxy}methyl)phenyl]-L-ornithinamide (Compd 5b)

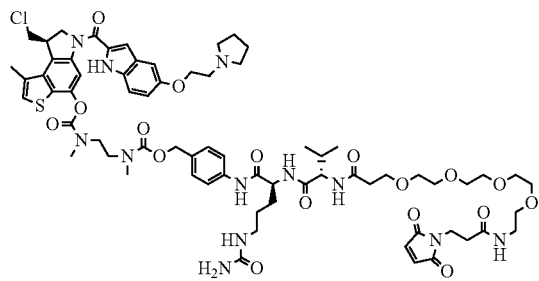 [SMILES: Cc1csc2c(OC(=O)N(C)CCN(C)C(=O)OCc3ccc(NC(=O)[C@H](CCCNC(N)=O)NC(=O)[C@@H](NC(=O)CCOCCOCCOCCOCCNC(=O)CCN4C(=O)C=CC4=O)C(C)C)cc3)cc3c(c12)[C@@H](CCl)CN3C(=O)c1cc2cc(OCCN3CCCC3)ccc2[nH]1]

The invention claimed is:
1. An intermediate compound of formula (XIa) or (XIb)

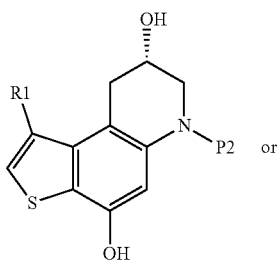
(XIa)

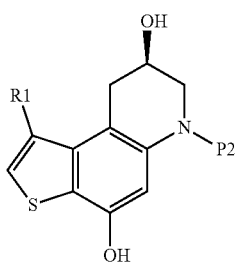
(XIb)

wherein:
R1 is hydrogen or linear or branched $C_1$-$C_6$ alkyl; and
P2 is a nitrogen protecting group.

2. An intermediate compound according to claim 1, wherein R1 is methyl and P2 is tert-butoxy carbonyl.

3. A process for preparing a compound of formula (XIa) or (XIb) wherein R1 and P2 are as defined in claim 1, which process comprises the steps of:
  a) N-alkylation of a compound of formula (VII) as defined in claim 1 with an enantiopure compound of formula (VIIIa) or (VIIIb) to give compounds of formula (IXa) or (IXb) respectively using strong basic conditions;
  b) intramolecular 6-endo-tet cyclization of the resulting compound of formula (IXa) or (IXb)

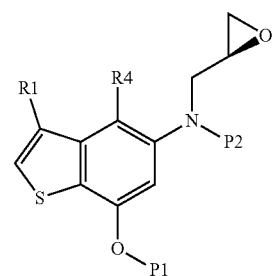
(IXa)

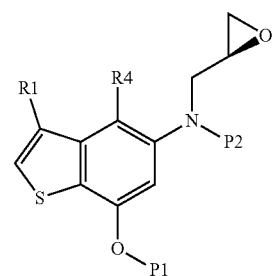
(IXb)

wherein R1 and P2 are as defined in claim 1, wherein R4 is halogen, and wherein P1 is a hydroxyl protecting group, with metallo-organic reagents and
  c) selective removal of the hydroxyl protecting group P1.

4. A process according to claim 3, wherein the metallo-organic reagent is selected from the group consisting of i-PrMgCl.LiCl, s-Bu₂MgLi.Cl, MeMgBr, i-prMgBr and EtMgBr.

5. A process according to claim 3, wherein the reaction of a compound of formula (IXa) or (IXb) with a metallo-organic reagent is carried out at a temperature ranging from −5° C. to 50° C. in an organic solvent selected from THF, Et₂O, DCM and mixtures thereof.

* * * * *